(12) United States Patent
Ido et al.

(10) Patent No.: US 8,934,101 B2
(45) Date of Patent: Jan. 13, 2015

(54) GAS ANALYSIS APPARATUS

(75) Inventors: Takuya Ido, Kyoto (JP); Toshikazu Ohnishi, Kyoto (JP); Tetsuya Mori, Otsu (JP)

(73) Assignee: Horiba, Ltd., Kyoto (JP)

( * ) Notice: Subject to any disclaimer, the term of this patent is extended or adjusted under 35 U.S.C. 154(b) by 0 days.

(21) Appl. No.: 14/238,520

(22) PCT Filed: Aug. 10, 2012

(86) PCT No.: PCT/JP2012/070461
§ 371 (c)(1),
(2), (4) Date: Feb. 12, 2014

(87) PCT Pub. No.: WO2013/024808
PCT Pub. Date: Feb. 21, 2013

(65) Prior Publication Data
US 2014/0211209 A1 Jul. 31, 2014

(30) Foreign Application Priority Data
Aug. 12, 2011 (JP) .................................. 2011-177339
Dec. 22, 2011 (JP) .................................. 2011-281515

(51) Int. Cl.
*G01N 21/61* (2006.01)
*G01N 21/35* (2014.01)
(Continued)

(52) U.S. Cl.
CPC ............ *G01N 21/61* (2013.01); *G01N 21/3504* (2013.01); *G01N 21/274* (2013.01);
(Continued)

(58) Field of Classification Search
USPC ........ 356/432, 436–439, 51, 71–73; 250/343, 250/341.1
See application file for complete search history.

(56) References Cited

U.S. PATENT DOCUMENTS

| 4,632,563 A | 12/1986 | Lord, III |
| 4,746,218 A | 5/1988 | Lord, III |

(Continued)

FOREIGN PATENT DOCUMENTS

| JP | 58-008147 A | 1/1983 |
| JP | 8-201290 A | 8/1996 |

(Continued)

OTHER PUBLICATIONS

International Preliminary Report on Patentability dated Feb. 18, 2014 for Corresponding PCT/JP2012/070461.

(Continued)

*Primary Examiner* — Sang Nguyen
(74) *Attorney, Agent, or Firm* — Brooks Kushman P.C.

(57) ABSTRACT

A gas analysis apparatus includes: a first reflector that reflects measurement light from a light emitting unit disposed outside a gas flue wall and transmitted through a sample gas. A light receiving unit outside the gas flue wall receives measurement light reflected by the first reflector. A second reflector outside the gas flue wall reflects measurement light toward the light receiving unit. A computing unit analyzes sample gas by allowing the measurement light to be reflected by the first reflector and performs correction or calibration of the gas analysis apparatus using known substances within an associated containing unit along the light path between the light emitting unit and the second reflector by allowing measurement light to be reflected by the second reflector. A switching unit outside the gas flue wall selectively removes or inserts the second reflector from the light path during component concentration analysis and correction or calibration, respectively.

18 Claims, 13 Drawing Sheets

(51) Int. Cl.
*G01N 21/27* (2006.01)
*G01N 21/53* (2006.01)
*G01N 21/85* (2006.01)

(52) U.S. Cl.
CPC .. *G01N2021/3513* (2013.01); *G01N 2021/536* (2013.01); *G01N 2021/8514* (2013.01); *G01N 2021/8578* (2013.01)
USPC .......................................... 356/437; 250/343

(56) References Cited

U.S. PATENT DOCUMENTS

| | | | |
|---|---|---|---|
| 5,625,189 A * | 4/1997 | McCaul et al. ................ | 250/343 |
| 5,673,109 A * | 9/1997 | Keilbach ........................ | 356/301 |
| 5,781,306 A | 7/1998 | Hartig et al. | |
| 5,929,981 A * | 7/1999 | Keilbach ......................... | 356/73 |
| 2006/0119851 A1 * | 6/2006 | Bounaix ......................... | 356/437 |
| 2009/0268204 A1 * | 10/2009 | Tkachuk ......................... | 356/437 |
| 2013/0003046 A1 * | 1/2013 | Izawa et al. .................... | 356/51 |

FOREIGN PATENT DOCUMENTS

| | | |
|---|---|---|
| JP | 11-133211 A | 5/1999 |
| JP | 2002048711 A | 2/2002 |
| JP | 2009098135 A | 5/2009 |
| JP | 2010185694 A | 8/2010 |

OTHER PUBLICATIONS

International Search Report mailed Nov. 20, 2012 for Corresponding PCT/JP2012/070461.

* cited by examiner

GAS ANALYSIS APPARATUS

CROSS REFERENCE TO RELATED APPLICATIONS

This application is the U.S. national phase of PCT/JP2012/070461 filed Aug. 10, 2012, which claims priority to Japanese Application 1011-177339 filed Aug. 12, 2011, and Japanese Application 2011-281515 filed Dec. 22, 2011, the disclosures of which are hereby incorporated by reference in their entirety.

TECHNICAL FIELD

The present invention relates to a gas analysis apparatus, particularly to a gas analysis apparatus that analyzes concentration of certain components in the sample gas using an optical absorption method.

BACKGROUND ART

Conventionally, exhaust combustion gas, which is exhausted from a boiler that burns coal or heavy oil, includes components such as $NO_x$, $SO_x$, $CO_2$, and CO. And a gas analysis apparatus has been developed that analyzes the contents of the components in the gas. As such a gas analysis apparatus, for example, an apparatus employing probe type has been developed. According to the gas analysis apparatus of probe type, measurement light is emitted from a light source, and the measurement light is reflected by a reflector arranged at a tip end of the probe. The apparatus analyzes constituent concentration of the sample gas based on information on the measurement light reflected by the reflector.

Some of the conventional gas analysis apparatus of probe type include zero correction function as well as the above-described component concentration analysis function. For example, one measurement light, which is emitted from the light source, is branched into two beams by an optical coupler and splitter, and one of the beams is used for analyzing the constituent concentration of the gas, and the other of the beams is used for the zero correction. The one beam used for analysis on constituent concentration of the gas and the beam used for the zero correction are input into different light receiving units and the signals are processed individually.

However, the above-described gas analysis apparatus includes problems below. The optical coupler and splitter have wavelength dependence, and cannot output the two beams in the same intensity after branching, depending on the wavelength band. In addition, the light receiving units have individual differences (differences among the devices) too, and the outputs may be actually different from each other in many cases, even though the light receiving units based on the same design are primarily intended to generate the same outputs in response to the same inputs. In addition, different signal processing units, which receive output from the light receiving unit, are employed for different light receiving units, so that the processing results by the signal processing units have some individual differences. Accordingly, in the signal processing result obtained based on the above-described two beams after the branch, there is a great chance of a difference resulting from the accumulation of each of the individual differences among the parts. Accordingly, it is impossible to accurately perform the zero correction, so that it is difficult to perform a highly accurate components analysis, which is a problem. Furthermore, it is necessary to have different systems (systems having a light receiving unit and a signal processing unit) for the two beams after the branch, so the whole analysis apparatus has to grow in size. In addition, the heating of the systems increases the heating value of the analysis apparatus as a whole, and the durability of the signal processing circuit is deteriorated, which is a problem. Since the gas analysis apparatus of probe type is attached to the flue for use, it is likely affected by heat of the sample gas and gets higher in temperature, so that it is likely to be deteriorated.

Furthermore, as a gas analysis apparatus of probe type, one that has calibration function as well as component concentration analysis function is disclosed in Patent Document 1. The gas analysis apparatus disclosed in Patent Document 1 includes a probe tube formed with an introduction hole through which the sample gas is introduced. According to the probe tube, most of its parts, including the tip end portion, is positioned inside of a gas flue wall (on a side of the gas flue), and only a base end portion is positioned outside the gas flue wall (on an opposite side of the gas flue). According to this gas analysis apparatus, the measurement light is emitted from the light source positioned outside the gas flue wall toward the sample gas in the probe tube. The measurement light is reflected by a first reflector arranged at a tip end portion of the tubular housing, and the reflected measurement light is received by a light receiving sensor arranged outside the gas flue wall. Based on information on the measurement light obtained at the light receiving sensor, the concentration of certain components contained in the sample gas can be calculated.

This gas analysis apparatus includes, as described above, a function of reflecting the measurement light emitted from the light source at the first reflector and analyzing the constituent concentration of the sample gas. The gas analysis apparatus further includes a function of reflecting the measurement light emitted from the light source at the second reflector and calibrating the gas analysis apparatus. The second reflector is positioned at a middle portion of the probe tube and inside of the gas flue wall. The position of the second reflector can be changed by a switching unit. The switching unit is positioned in a middle portion of the probe tube and inside of the gas flue wall, and is configured to move the second reflector out of a light path when analyzing the component concentration and to place the second reflector into the light path when performing the calibration. According to the switching operation by the switching unit, it is possible to selectively perform the analysis of constituent concentration of the gas and the calibration for the gas analysis apparatus.

CITATION LIST

Patent Literature

Patent Citation: U.S. Pat. No. 5,781,306

SUMMARY OF INVENTION

Technical Problem

The present invention was conceived considering the above-described circumstances, it is an object of the present invention to provide an analysis apparatus that is compact and can reduce the manufacturing cost and the maintenance cost, as well as having excellent concentration analysis accuracy.

Solution to Problem

According to one aspect of the present invention, a gas analysis apparatus is configured to analyze concentrations of element gases in a sample gas flowing in a flue. The gas analysis apparatus includes a light-emitting unit, a first reflector, a light-receiving unit, a second reflector, a known substance containing unit, a computing unit, and a switching unit.

The light-emitting unit is arranged outside a wall of the flue and configured to apply a measurement light to the sample gas.

The first reflector is configured to reflect the measurement light applied from the light-emitting unit and that has been transmitted through the sample gas.

The light-receiving unit is arranged in the vicinity of the light-emitting unit and outside the wall of the flue, and configured to receive the measurement light reflected by the first reflector.

The second reflector is arranged outside the wall of the flue and configured to reflect the measurement light to the light-receiving unit.

The known substance containing unit is arranged in a space region along a light path between the light-emitting unit and the second reflector and between the second reflector and the light receiving unit. The known substance containing unit contains a known substance that does not attenuate the measurement light emitted from the light-emitting unit or attenuates the measurement light by a predetermined amount.

The computing unit is configured both to analyze the concentrations of the element gases in the sample gas using the measurement light reflected by the first reflector. The computing unit is configured to perform at least one of a correction and a calibration with the known substance using the measurement light reflected by the second reflector.

The switching unit is arranged outside the wall of the flue and configured to remove the second reflector from the light path when performing the analysis of the concentrations of the element gases and to place the second reflector into the light path when performing at least one of the correction and the calibration.

"Known substance" can be any substance in which, when applied with the measurement light, the amount of transmitted light is known in advance. In other words, "known substance" includes, for example, zero gas and span gas, as well as an optically transparent plate and an optical element which may be optically transparent perfectly for the measurement light or which may limit the transmitted measurement light to a fixed amount.

Furthermore, "correction" includes zero correction in which the measurement light is applied by the light emitting unit to the known substance, and the measurement light that has been transmitted through the known substance is received. "Calibration" includes zero calibration and span calibration in which the measurement light is applied by the light emitting unit to the known substance, and the measurement light that has been transmitted through the known substance is received.

In addition, "does not attenuate the measurement light" means that the measurement light is completely transmitted. One of the known substances having such characteristics is zero gas, for example.

According to this apparatus, since the second reflector and the switching unit are arranged outside the gas flue wall, these parts are not exposed to the sample gas having a high temperature. Accordingly, it is possible to suppress the deterioration of the second reflector and the switching unit, and suppress the frequency of replacing parts, thereby reducing the maintenance cost. In addition, the switching operation by the switching unit allows the apparatus to be set selectively in a state of removing the second reflector from the light path or in a state of placing the second reflector into the light path. Accordingly, it is possible to perform the component concentration analysis, the zero correction, the zero calibration, the span calibration, and so on, with one light receiving unit, without allowing one beam to be branched into two light beams by the optical coupler and splitter. As a result, it is possible to perform the component concentration analysis highly accurately, not being affected by the individual differences due to providing the two light receiving units as in the conventional arts. In addition, it is possible to perform the component concentration analysis, the zero correction, the zero calibration, the span calibration, and so on, with one system (a system consisting of the light receiving unit and the signal processing unit). Accordingly, it is possible to realize a gas analysis apparatus as a whole with small number of parts and to make it compact, thereby suppressing the manufacturing cost. In addition, since the second reflector and the switching unit are arranged outside the gas flue wall, it is easy to exchange these parts.

The switching unit may include a back-forward moving mechanism configured to remove the second reflector from the light path and to place the second reflector into the light path.

In this apparatus, by moving the second reflector forward and backward, it is possible to remove the second reflector from the light path, and to place the second reflector into the light path. In other words, it is possible to reliably switch the positions of the second reflector with a simple mechanism.

The second reflector, when placed in the light path, may serve as a shutter that separates a space near the flue from a space near the known substance containing unit.

The back-forward moving mechanism may include an air cylinder or a motor.

The back-forward moving mechanism may include a positioning mechanism configured to arrange the second reflector in a same direction and at a same position every time when the second reflector is placed into the light path through an operation of the air cylinder or the motor.

In this apparatus, when the second reflector is returned into the light path by force from the air cylinder or the motor, the second reflector is positioned in the same orientation and at the same position by the positioning mechanism. In this case, the complicated structure for positioning or a special energy source becomes unnecessary, thereby reducing the cost.

The positioning mechanism may include a holder fixed to the second reflector and a bearing configured to hold the holder. The bearing may have a conical concave. The holder may have a conical or spherical convex. The concave may have a first plane with a trapezoidal shape that is formed in a part of the concave. A side of the first plane at a bottom of the concave may be narrower than that at a top of the concave. The convex may have a second plane configured to abut against the first plane in a complementary manner.

In this apparatus, if the air cylinder or the motor pushes the second reflector and the holder toward the bearing, the convex of the holder fits into the concave of the bearing. At this time, the above-described shape makes it possible for the convex to approach the concave while the convex is allowed to move in the rotational direction. Then, finally, the second plane of the convex abuts against the first plane of the concave in a complementary manner. In this state, the convex can neither move relative to the concave in the moving direction nor in the rotational direction anymore. Accordingly, the second reflector is always positioned in the same direction and at the same position.

The known substance containing unit may include an optically transparent cell.

The gas analysis apparatus may further include a probe tube with a cylindrical shape having introduction openings through which the sample gas is introduced into the probe tube. The light-emitting unit may apply the measurement light to the sample gas in the probe tube.

In this apparatus, the present invention can be applied to the gas analysis apparatus of probe type, which makes it easier to attach the apparatus to the wall, and to maintain and manage the apparatus.

The probe tube may include a front end portion placed inside the wall and a base end portion placed outside the wall. The first reflector may be arranged at the front end portion of the probe tube, and the second reflector may be arranged at the base end portion of the probe tube.

In this apparatus, since the second reflector is positioned at the base end portion of the probe tube (i.e., outside the gas flue wall), when exchanging the second reflectors, it is possible to easily exchange them without extracting the probe from the gas flue.

The known substance containing unit may be placed at the base end portion of the probe tube.

The first reflector may be arranged outside the wall that is opposite to a portion where the second reflector is arranged in the flue.

In this apparatus, the present invention can be applied to a gas analysis apparatus of open-path type, in which the first reflector is positioned outside of the wall, on the opposite side of the second reflector in the gas flue.

Advantageous Effects of Invention

According to the present invention, it is possible to provide a gas analysis apparatus, which is compact and can reduce the manufacturing cost and the maintenance cost, and have excellent analytical accuracy.

DESCRIPTION OF EMBODIMENTS

First Embodiment

Figure 1:
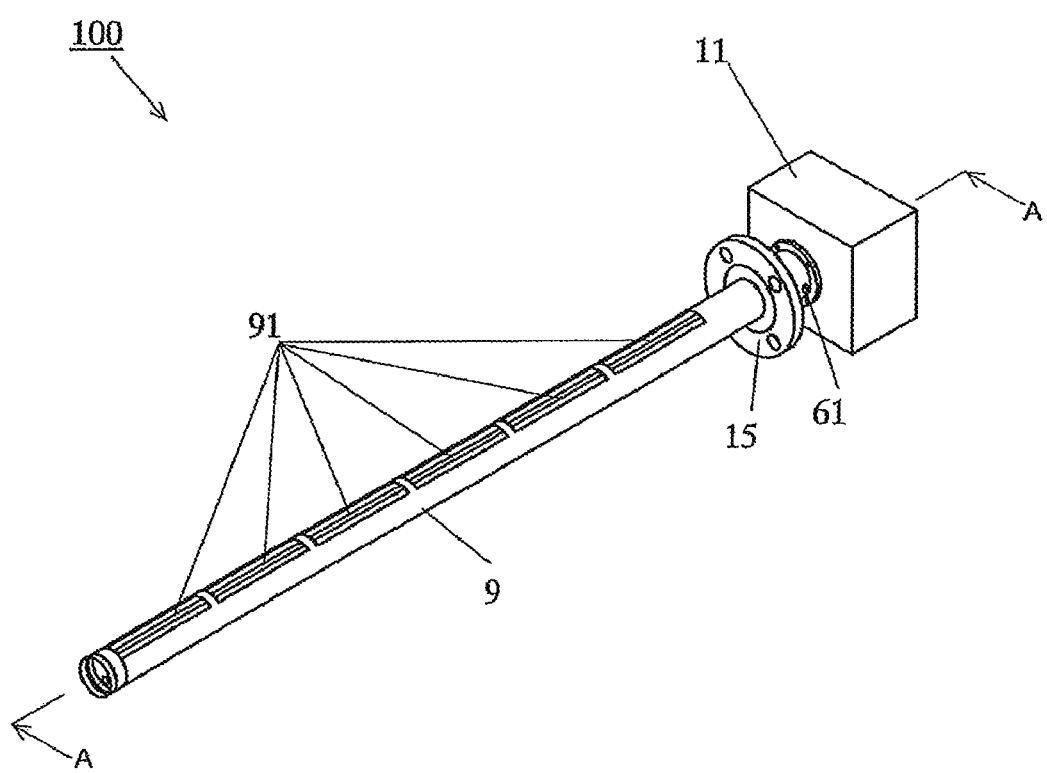
FIG. 1 is an outside view of a gas analysis apparatus according to a first embodiment.
Figure 2:
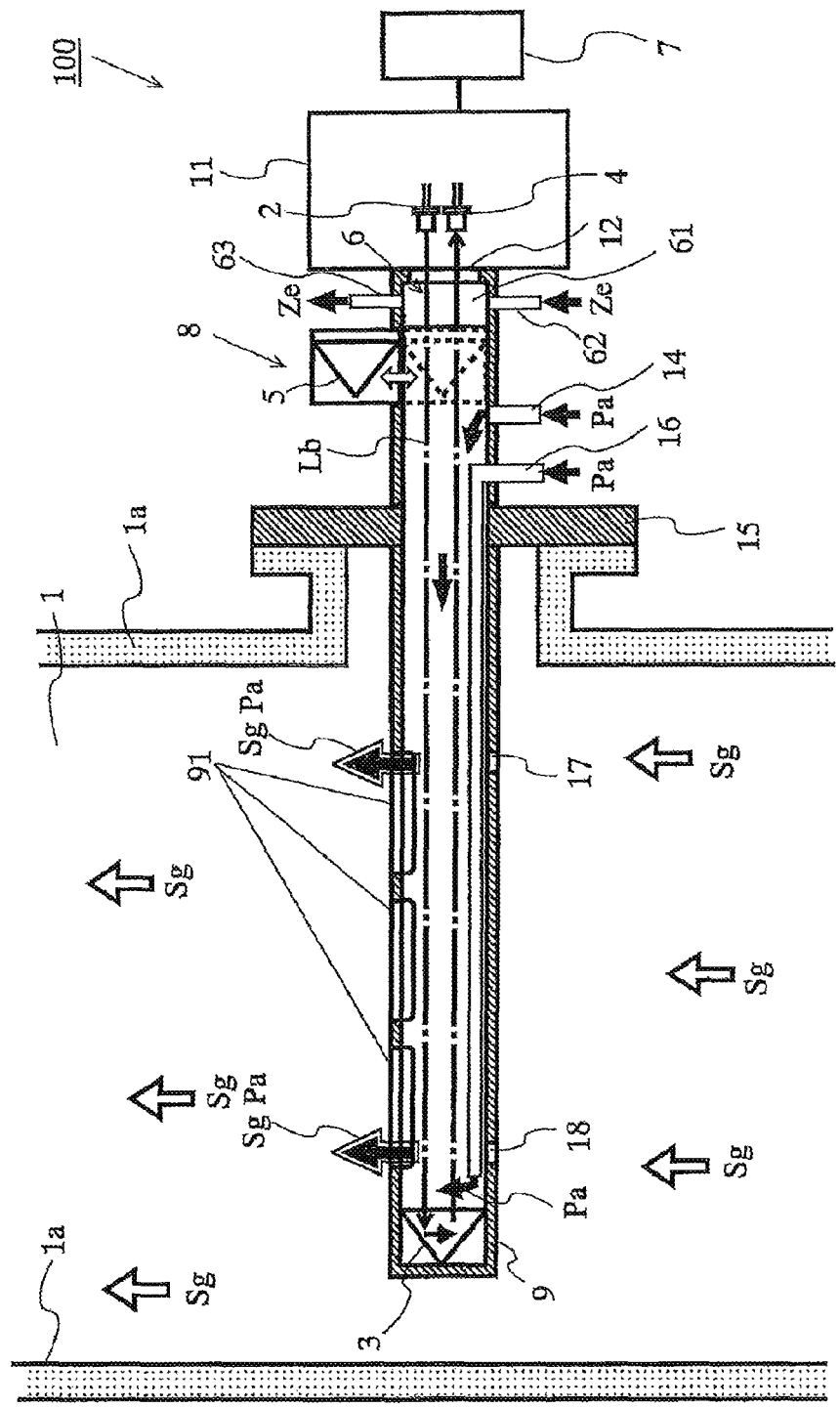
FIG. 2 is a view including A-A section of the gas analysis apparatus shown in FIG. 1, and is a view for showing the gas concentration analysis mode.
Figure 3:
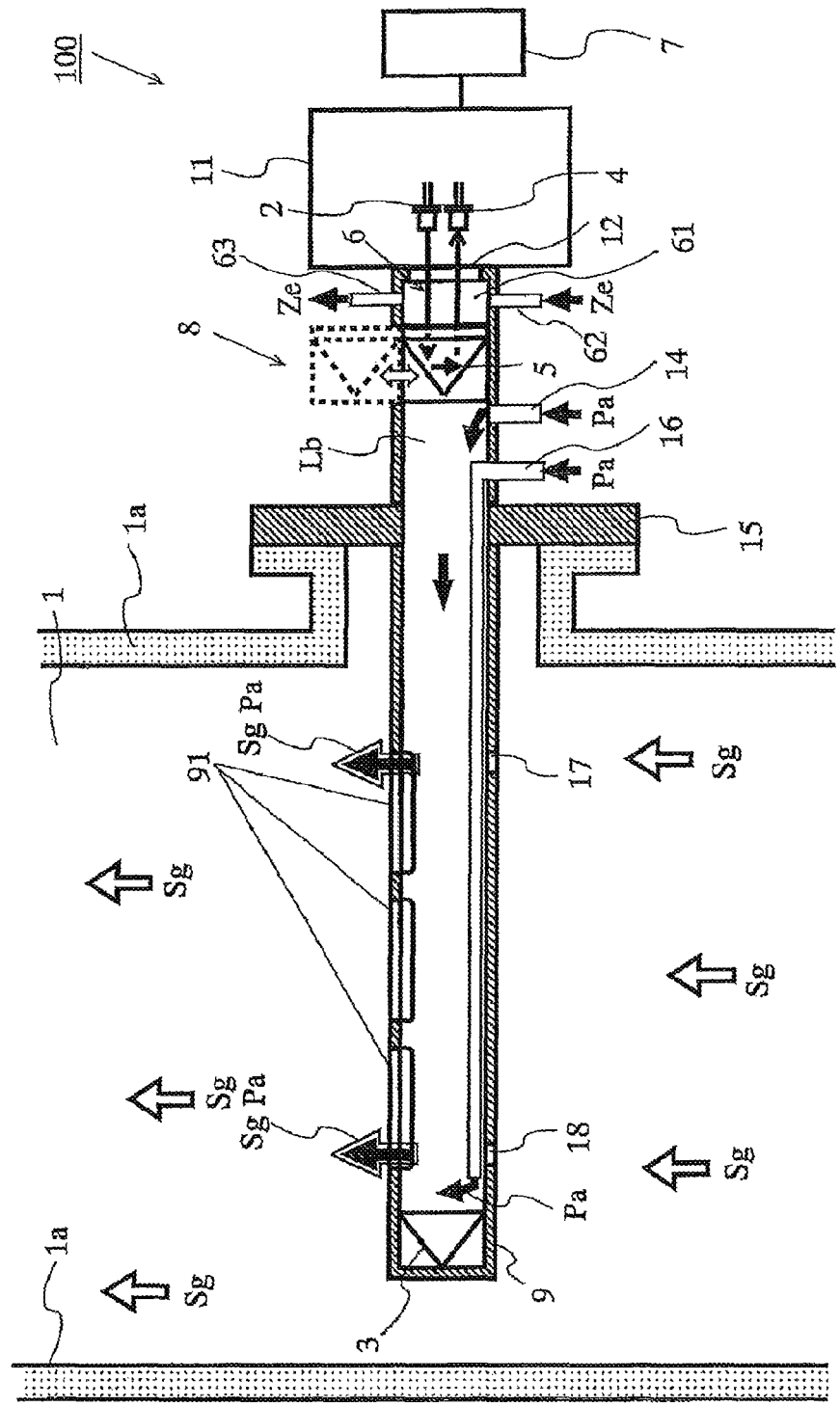
FIG. 3 is a view including A-A section of the gas analysis apparatus shown in FIG. 1, and is a view for showing the correction mode or the calibration mode.

Below, a gas analysis apparatus 100 according to the first embodiment will be described. The gas analysis apparatus 100 is what is called a gas analysis apparatus of probe type. FIG. 1 is an outside view of a gas analysis apparatus according to a first embodiment. FIG. 2 is a view including A-A section of the gas analysis apparatus shown in FIG. 1, and is a view for showing the gas concentration analysis mode. FIG. 3 is a view including A-A section of the gas analysis apparatus shown in FIG. 1, and is a view for showing the correction mode or the calibration mode.

The gas analysis apparatus 100 according to the first embodiment is a gas analysis apparatus that analyzes concentration of certain components contained in the sample gas flowing into a gas flue 1. The gas analysis apparatus 100 is, for example, a non-dispersive infrared (NDIR) analyzer.

As shown in FIGS. 2, 3, the gas analysis apparatus 100 includes one light emitting unit 2, a first reflector 3, one light receiving unit 4, a second reflector 5, a known substance containing unit 6, a computing unit 7, a switching unit 8, and a probe tube 9. The first reflector 3, the second reflector 5, and the known substance containing unit 6 are accommodated in the probe tube 9. The light emitting unit 2 and the light receiving unit 4 constitute an optical unit, and are accommodated in a housing 11 of the optical unit. At a connecting part between the cabinet 11 and the probe tube 9, an optical window 12 is arranged. The optical window 12 is a plate member made of materials through which the measurement light Lb may be transmitted.

The probe tube 9 is a cylindrical member formed with introduction holes 91 for introducing sample gas Sg into the probe tube 9 by diffusion. The material of the probe tube 9 can be any metallic materials depending on usage environment of the gas analysis apparatus 100. The introduction hole 91 is, as shown in FIG. 1, for example, continual slits on the side surface of the probe tube 9. At the tip end portion in the probe tube 9, as shown in FIG. 2, the first reflector 3 is provided. In contrast, at base end portion in the probe tube 9, the second reflector 5 and the known substance containing unit 6 are provided.

The probe tube 9 is fixed to the gas flue wall 1a by means of a flange 15. The flange 15 is a member for fixing the gas analysis apparatus 100 to the wall 1a of the gas flue that exhausts the sample gas Sg or a container in which the sample gas Sg is contained with a seal. The flange 15 is, for example, a disc-shaped member, and is provided on a side of the probe tube 9 towards the base end portion (a side connected to the optical unit) so as to be penetrated through by the probe tube 9. The flange 15 is fastened to the gas flue wall 1a by bolts, for example. The portion of the probe tube 9 past the flange 15 towards the tip end is provided inside of the gas flue wall 1a, and the portion of the probe tube 9 towards the base end from the flange 15 is provided outside the gas flue wall 1a.

Material, shape, and position of the probe tube are not limited. In addition, position, shape, and the number of the introduction holes formed in the probe tube are not limited.

The light emitting unit 2 is arranged outside the gas flue wall 1a that constitutes the tubular gas flue 1, and is configured to emit the measurement light Lb into the sample gas Sg flowing through the probe tube 9. The light emitting unit 2 is, typically, a light source device that emits light in a certain wavelength region having high rectilinear advancing property, such as an infrared laser oscillating apparatus.

The first reflector 3 is configured to reflect the measurement light Lb, which has been emitted from the light emitting unit 2 and has been transmitted through the probe tube 9, toward the light receiving unit 4. In other words, the first reflector 3 is a means for changing the direction of the light (optical axis) emitted from the light emitting unit 2 toward the light receiving unit 4, and is a corner cube, for example. In an example shown in FIG. 2, it is a corner cube prism. It should be noted that the first reflector 3 may be a corner cube mirror.

The light receiving unit 4 is arranged in the vicinity of the light emitting unit 2 and outside the gas flue wall 1a. The light receiving unit 4 is configured to receive the measurement light Lb that has been reflected by the first reflector 3. The light receiving unit 4 is a light receiving device configured to receive the measurement light Lb on a light receiving surface thereof. The light receiving unit 4 is typically a photoelectric conversion device such as a photodiode. The light receiving unit 4 is electrically connected to the computing unit 7, and is configured to send the information on the received measurement light Lb (e.g., quantity of light) as electric signals to the computing unit 7.

The second reflector 5 is arranged outside the gas flue wall 1a, and is configured to reflect the measurement light Lb toward the light receiving unit 4. In other words, the second reflector 5 is a means for changing the direction of the light (optical axis) emitted from the light emitting unit 2 toward the light receiving unit 4, and is a corner cube, for example. In an example shown in FIG. 2, it is a corner cube prism. It should be noted that the second reflector 5 may be a corner cube mirror.

The known substance containing unit 6 is arranged at a space region along a light path between the light emitting unit 2 and the second reflector 5 as well as between the second reflector 5 and the light receiving unit 4. The known substance containing unit 6 contains a known substance that does not attenuate the measurement light Lb emitted from the light emitting unit 2 or attenuates the measurement light Lb by a predetermined amount. Here, "known substance" can be any substance in which, when applied with the measurement light Lb, the amount of transmitted light is known in advance. In other words, "known substance" includes zero gas and span gas, and further includes an optically transparent plate or an optical element, for example, which may be completely transparent for the measurement light or which may limit the transmitted measurement light to a fixed amount. In an example shown in FIGS. 2, 3, the known substance containing unit 6 is configured to contain a known gas (zero gas or span gas) to correct or calibrate the gas analysis apparatus 100. The known substance containing unit 6 can be constituted, for example, by an optically transparent cell 61, a gas introduction pipe 62 for supplying the known gas into the cell 61, and a gas exhaustion pipe 63 for exhausting the known gas in the cell 61. In the first embodiment, "correction" means performing zero correction, for example. In addition, "calibration" means performing zero calibration or span calibration, for example. The zero gas is a reference gas for correcting the zero point of the gas analysis apparatus 100, and may be nitrogen, for example.

It should be noted that the structure of the known substance containing unit 6 is not limited to the above-described one. The known substance containing unit 6 may be constituted by introducing and filling the known gas into a space region between the optical window 12 and the second reflector 5 while the second reflector 5 is placed in the light path, without providing the optically transparent cell 61, for example. When performing the calibration, the span gas is introduced into the known substance containing unit 6, or the zero gas and the span gas are alternately introduced into the known substance containing unit 6.

The computing unit 7 (arithmetic processing unit) is configured to control the operation of the light emitting unit 2, the light receiving unit 4, and the switching unit 8. Furthermore, the computing unit 7 is configured to analyze component concentration of the sample gas Sg in the probe tube 9 based on the signals received from the light receiving unit 4 after the measurement light Lb emitted from the light emitting unit 2 is reflected by the first reflector 3. The computing unit 7 is configured to correct or calibrate the gas analysis apparatus 100 using the known gas, by reflecting the measurement light Lb at the second reflector 5 which has been emitted from the light emitting unit 2.

The computing unit 7 typically includes an information processing unit such as CPU (Central Processing Unit), storage devices such as memory, interface devices for receiving user operations, and a display device for displaying the result of analysis. The computing unit 7 performs a computing process based on user operations and programs stored in the storage device.

It should be noted that the above-described plurality of functions of the computing unit 7 may be realized by a single information processing device, or may be realized by a plurality of information processing units.

Figure 4:
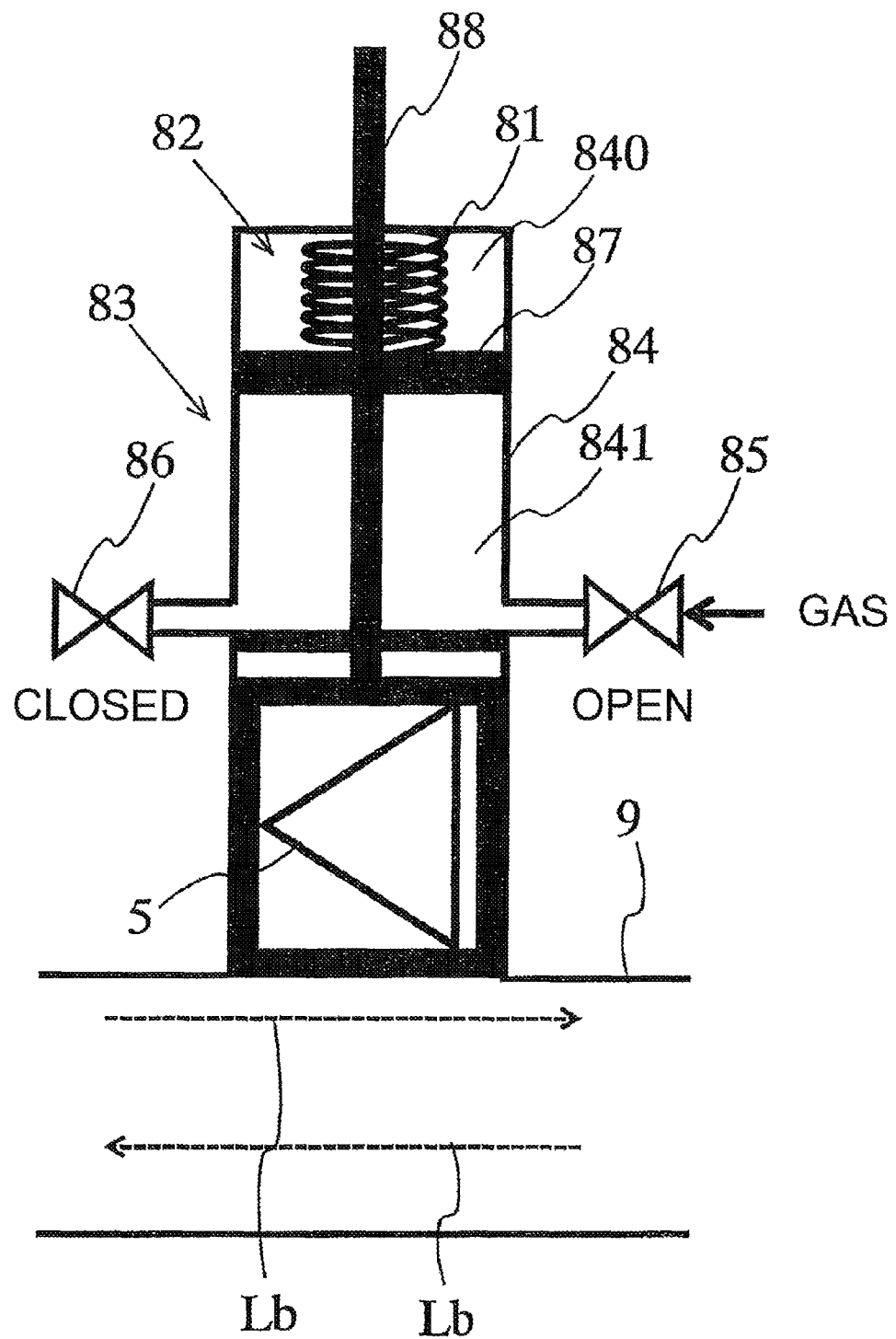
FIG. 4 is a sectional view showing a structure of a switching unit in the first embodiment, and is a view for showing the gas concentration analysis mode.
Figure 5:
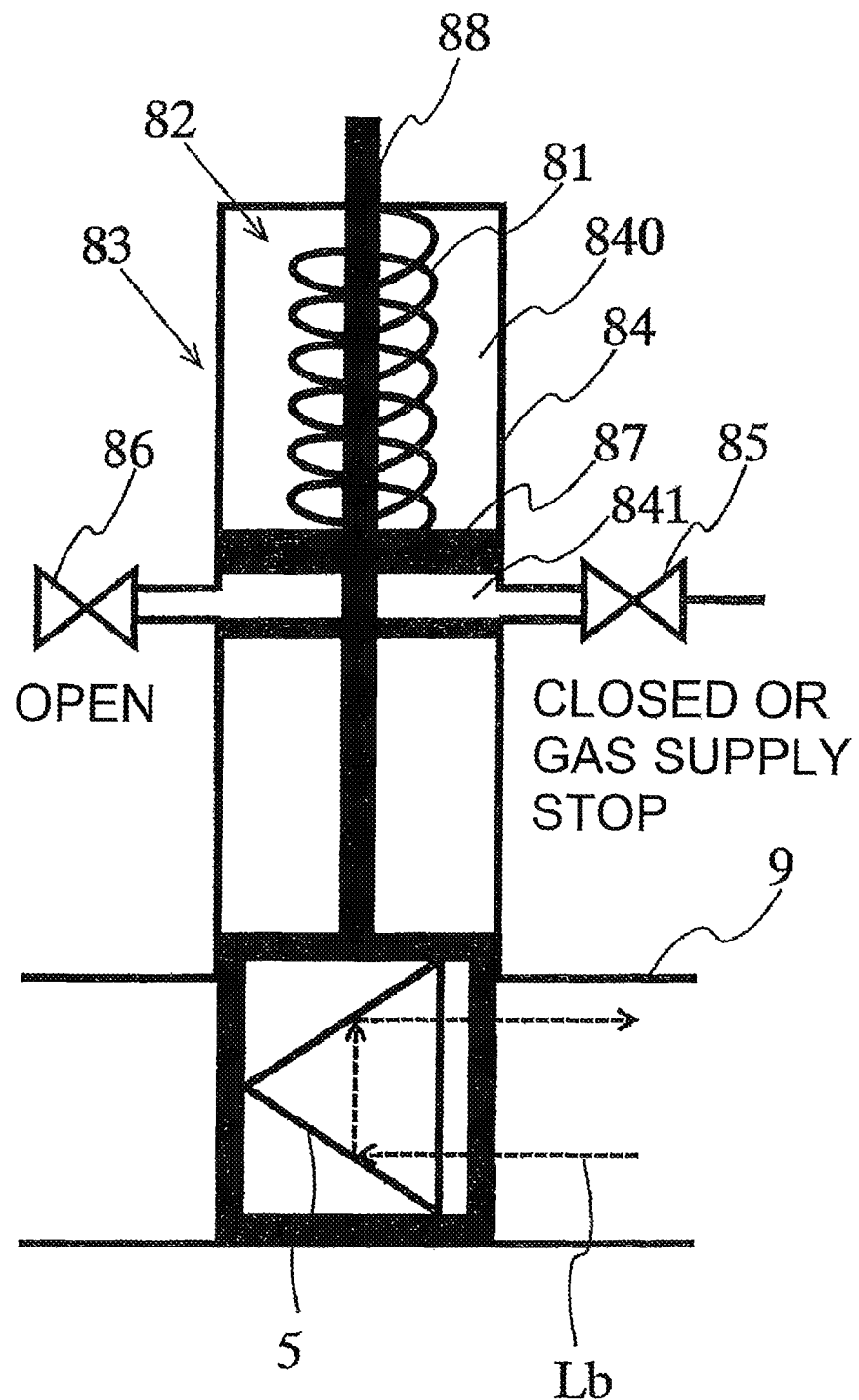
FIG. 5 is a sectional view for showing a structure of the switching unit in the first embodiment, and is a view for showing the correction mode or the calibration mode.

The switching unit 8 is arranged outside the gas flue wall 1a, and is configured to remove the second reflector 5 from the light path when the component concentration is to be analyzed (refer to FIGS. 2, 4) and to dispose the second reflector 5 into the light path when the correction or the calibration is to be performed (refer to FIGS. 3, 5).

The structure of the switching unit 8 is not particularly limited, but can be a structure shown in FIGS. 4, 5, for example. FIG. 4 is a sectional view showing an example of a structures of the switching unit 8, and is a view for showing the gas concentration analysis mode. FIG. 5 is a sectional view for showing an example of structures of the switching unit 8, and is a view for showing the correction mode or the calibration mode. In an example shown in FIGS. 4, 5, the switching unit 8 includes a back-forward moving mechanism configured to remove the second reflector 5 from the light path, and place it into the light path. The back-forward moving mechanism includes a spring mechanism 82 configured to place the second reflector 5 into the light path by elastic force of a spring 81, and an air pressure mechanism 83 configured to remove the second reflector 5 from the light path by air pressure while resisting the elastic force of the spring 81.

The air pressure mechanism 83 includes an air cylinder 84, a supply valve 85, an exhaust valve 86, a piston 87, and a rod 88. The air cylinder 84 is provided above the second reflector 5. The supply valve 85 supplies the air pressure to the air cylinder 84. The exhaust valve 86 exhausts the air in the air cylinder 84. The air cylinder 84 has two air chambers with the piston 87 therebetween. The first air chamber 840 is defined between an end portion near the base end of the air cylinder 84 and the piston 87, and the spring 81 of compression coil type is arranged in the first air chamber 840. No spring is arranged in a second air chamber 841. The supply valve 85 and the exhaust valve 86 are connected to the second air chamber 841, and supply the air to the second air chamber 841 from a compressor, and exhaust the air in the second air chamber 841.

As shown in FIG. 4, when the supply valve 85 is opened and the exhaust valve 86 is closed, the air flows into the second air chamber 841 from the compressor through the supply valve 85. As a result, the air pressure in the second air chamber 841 increases. If the force due to the air pressure becomes higher than the elastic force of the spring 81, the spring 81 is compressed and the piston 87 ascends. Due to the ascending of the piston 87, the second reflector 5 connected to the rod 88 ascends, so that the second reflector 5 is removed from the light path.

In contrast, if the supply valve 85 is closed and the exhaust valve 86 is opened as shown in FIG. 5, the air from the compressor is shut off by the supply valve 85, so that the air pressure in the second air chamber 841 decreases. If the elastic force of the spring 81 becomes larger than the force by the air pressure, the spring 81 extends and the piston 87 descends. Due to the descending of the piston 87, the second reflector 5 connected to the rod 88 descends, so that the second reflector 5 is placed into the light path.

Furthermore, as shown in FIG. 5, if the air supply from the compressor is shut off due to abnormality such as a power failure, even if the supply valve 85 is open, the air pressure in the second air chamber 841 decreases. If the elastic force of the spring 81 becomes larger than the force by the air pressure, the spring 81 extends and the piston 87 descends. Due to the descending of the piston 87, the second reflector 5 connected to the rod 88 descends, so that the second reflector 5 is placed into the light path. Since the second reflector 5 performs a function of a shutter for blocking the inside of the probe tube 9, it is possible to prevent the sample gas Sg from intruding into a region near the light emitting unit 2.

Figure 6:
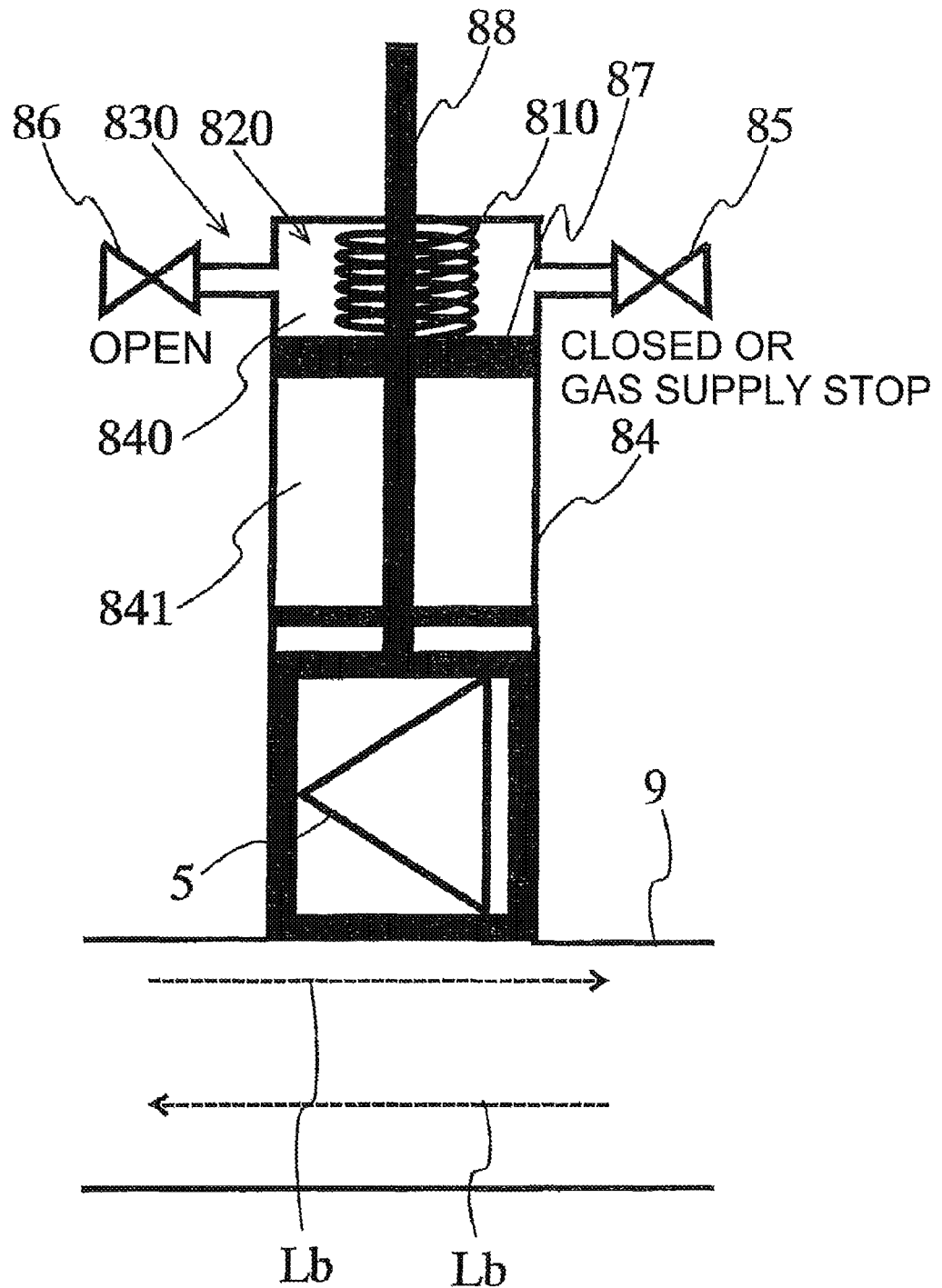
FIG. 6 is a sectional view for showing another structure of the switching unit in the first embodiment, and is a view for showing the gas concentration analysis mode.
Figure 7:
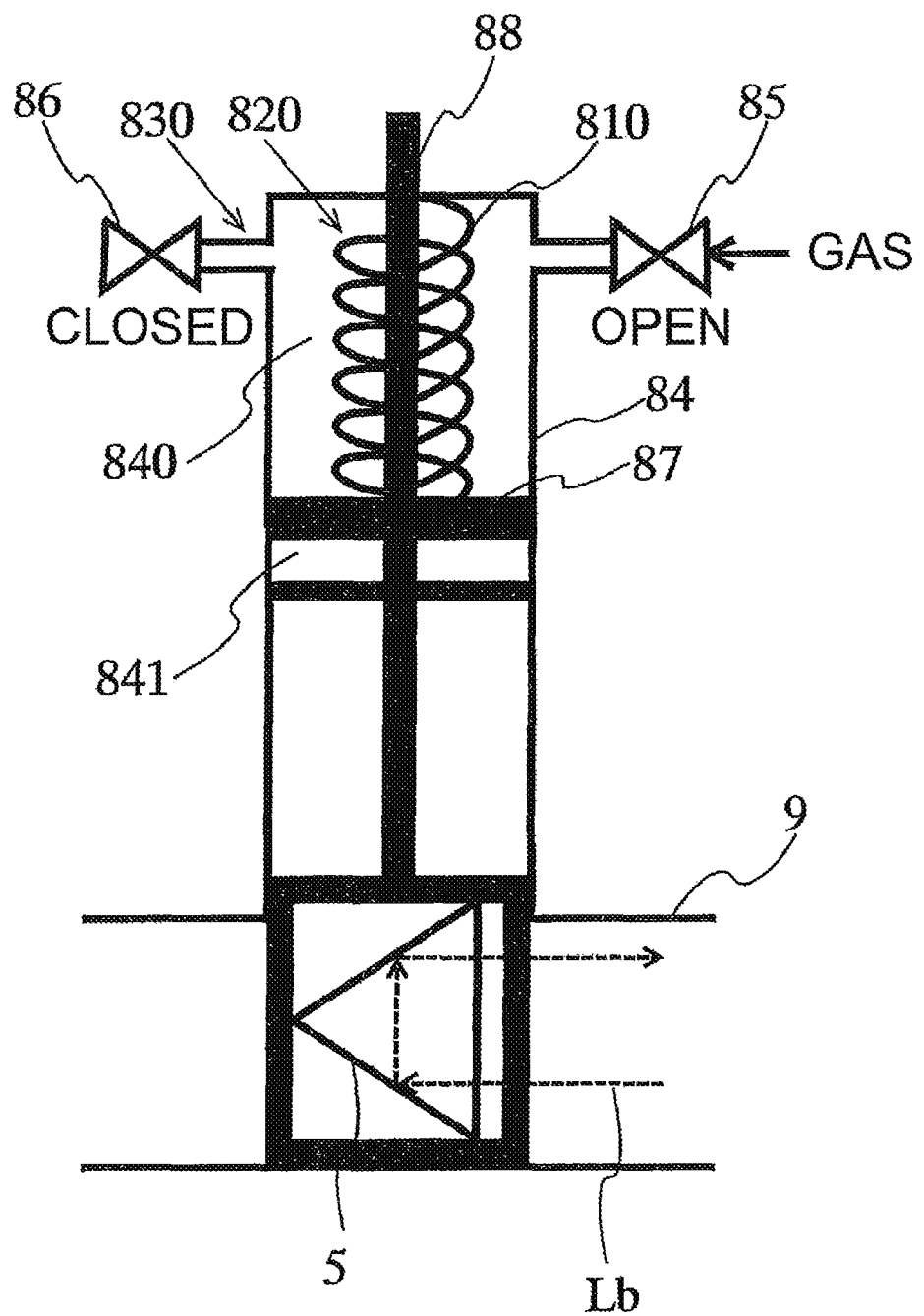
FIG. 7 is a sectional view for showing another structure of the switching unit in the first embodiment, and is a view for showing the correction mode or the calibration mode.

Since it is essential only that the switching unit 8 is arranged outside the gas flue wall 1*a*, various modifications can be employed. For example, the structure of the switching unit 8 can be one shown in FIGS. 6, 7 instead of the above-described one. FIG. 6 is a sectional view for showing another structure of the switching unit 8, and is a view for showing the gas concentration analysis mode. FIG. 7 is a sectional view for showing another structure of the switching unit 8, and is a view for showing the correction mode or the calibration mode. According to the example shown in FIGS. 6, 7, the switching unit 8 includes a back-forward moving mechanism that removes the second reflector 5 from the light path and places the second reflector 5 into the light path. The back-forward moving mechanism includes a spring mechanism 820 configured to remove the second reflector 5 from the light path with an elastic force of the spring 810, and an air pressure mechanism 830 configured to place the second reflector 5 by the air pressure against the elastic force of the spring 810 into the light path.

The air pressure mechanism 830 includes an air cylinder 84, a supply valve 85, an exhaust valve 86, a piston 87, and a rod 88. The air cylinder 84 is provided above the second reflector 5. The supply valve 85 is configured to supply the air pressure to the air cylinder 84. The exhaust valve 86 is configured to exhaust the air in the air cylinder 84. The air cylinder 84 includes two air chambers with the piston 87 therebetween. A first air chamber 840 is defined between an end portion near the base end of the air cylinder 84 and the piston 87, and an extension coil spring 810 is arranged in the first air chamber 840. No spring is arranged in a second air chamber 841. The supply valve 85 and the exhaust valve 86 are connected to the first air chamber 840, and supply the air from the compressor into the first air chamber 840, and exhaust the air in the first air chamber 840.

As shown in FIG. 6, if the supply valve 85 is closed and the exhaust valve 86 is opened, the air from the compressor is shut off by the supply valve 85, so that the air pressure in the first air chamber 840 decreases. If the elastic force of the spring 810 becomes larger than the force by the air pressure, the spring 810 is contracted and the piston 87 ascends. Due to the ascending of the piston 87, the second reflector 5 connected to the rod 88 ascends, so that the second reflector 5 is removed from the light path.

In addition, as shown in FIG. 6, if the supply of the air from the compressor is shut off due to abnormality such as a power failure, even if the supply valve 85 is open, the air pressure in the first air chamber 840 decreases. If the elastic force of the spring 810 becomes larger than the force by the air pressure, the spring 810 is contracted and the piston 87 ascends. Due to the ascending of the piston 87, the second reflector 5 connected to the rod 88 ascends, and the second reflector 5 is removed from the light path.

In contrast, if the supply valve 85 is opened and the exhaust valve 86 is closed as shown in FIG. 7, the air from the compressor is supplied through the supply valve 85 to the first air chamber 840. As a result, the air pressure in the first air chamber 840 increases. If the force by the air pressure becomes larger than the elastic force of the spring 810, the spring 810 extends and the piston 87 descends. Due to the descending of the piston 87, the second reflector 5 connected to the rod 88 descends, so that the second reflector 5 is placed into the light path.

In the above-described probe tube 9, as shown in FIG. 2, a purge air introduction port 14 is provided to introduce the purge air Pa into the probe tube 9. The purge air introduction port 14 is, as shown in FIG. 2, provided outside the gas flue wall 1*a* and on a side of the second reflector 5 near the gas flue, for example. Through the purge air introduction port 14 arranged as previously mentioned, the purge air Pa is introduced with a certain pressure to prevent the sample gas Sg and dust in the probe tube 9 from contacting the optical window 12, so that it is possible to reduce contamination and corrosion of the optical window 12. It should be noted that an image of the flow path of the purge air Pa is shown with black and bold arrows in FIG. 2, and an image of the flow path of the sample gas Sg is shown with white arrows in FIG. 2.

Furthermore, the probe tube 9 includes a purge air introduction pipe 16 configured to introduce the purge air Pa to the front surface of the first reflector 3 for protection. According to this structure, it is possible to prevent the sample gas Sg and the dust in the probe tube 9 from contacting the first reflector 3, so that contamination and corrosion of the first reflector 3 can be reduced.

In addition, as shown in FIG. 2, the probe tube 9 is formed with holes 17, 18 near two ends, on a side (upstream side of the flow of the sample gas Sg) opposite to the introduction hole 91. Since the sample gas Sg flows through the holes 17, 18, it is possible to prevent the purge air Pa from flowing into the central portion of the probe tube 9, so that the purge air Pa is mixed with the sample gas Sg and then is exhausted from the introduction hole 91 (SgPa). The introduction hole 91 is used also as an exhaust port for exhausting the purge air Pa.

Next, use of the gas analysis apparatus 100 will be described.

First, a case will be explained in which a normal gas concentration analysis is performed.

A user gives an instruction to the computing unit 7 for performing the gas concentration analysis. Then, as shown in FIGS. 2, 4, the switching unit 8 removes the second reflector 5 from the light path of the measurement light Lb emitted from the light emitting unit 2. The measurement light Lb emitted from the light emitting unit 2 is transmitted through the sample gas Sg in the probe tube 9, and is reflected by the first reflector 3. The reflected measurement light Lb is transmitted through the sample gas Sg again and is received by the light receiving unit 4. Part of the measurement light Lb is absorbed by the sample gas Sg when the measurement light Lb is transmitted through the sample gas Sg. The computing unit 7 acquires the amount of absorption of the measurement light Lb in the sample gas Sg, based on difference between information on the measurement light Lb obtained at the light receiving unit 4 and information on of the measurement light Lb when it is emitted from the light emitting unit 2. The computing unit 7 then calculates concentration of certain components contained in the sample gas Sg based on the amount of absorption.

Next, a case will be explained in which the correction (zero correction) is performed.

A user gives an instruction to the computing unit 7 for performing the correction. Then, as shown in FIGS. 3, 5, the switching unit 8 places the second reflector 5 into the light path of the measurement light Lb emitted from the light emitting unit 2. The measurement light Lb emitted from the light emitting unit 2 is transmitted through the zero gas supplied into the known substance containing unit 6, and is reflected by the second reflector 5. The reflected measurement light Lb is transmitted through the zero gas in the known substance containing unit 6 again and is received by the light receiving unit 4. The computing unit 7 can calculate a reference value of the zero correction, based on difference between information on the measurement light Lb obtained at the light receiving unit 4 and information on the measurement light Lb when it is emitted from the light emitting unit 2. The computing unit 7 performs the zero correction of the gas analysis apparatus 100 using the calculated reference value. The zero correction is preferably performed at an interval of one hour, for example. The zero correction can be performed each time a user instruction is given, or can be performed automatically and periodically.

Next, a case is explained in which the calibration is performed. Here, an example will be explained in which both the zero correction and the span calibration are performed.

In order to perform the zero correction and the span calibration, the zero gas and the span gas are alternately supplied into the known substance containing unit 6. Then, as shown in FIGS. 3, 5, the switching unit 8 places the second reflector 5 into the light path of the measurement light Lb emitted from the light emitting unit 2. When the zero gas is introduced, the measurement light Lb emitted from the light emitting unit 2 is transmitted through the zero gas supplied into the known substance containing unit 6, and is reflected by the second reflector 5. The reflected measurement light Lb is transmitted through the zero gas in the known substance containing unit 6 again, and is received by the light receiving unit 4. The computing unit 7 calculates a reference value of the zero correction, based on difference between information on the measurement light Lb obtained by the light receiving unit 4 and information on the measurement light Lb emitted from the light emitting unit 2. And, when the span gas is introduced, the measurement light Lb emitted from the light emitting unit 2 is transmitted through the span gas supplied into the known substance containing unit 6, and is reflected by the second reflector 5. Then, the reflected measurement light Lb is transmitted through the span gas in the known substance containing unit 6 again, and is received by the light receiving unit 4. The computing unit 7 calculates a reference value for the span calibration, based on difference between information on the measurement light Lb obtained at the light receiving unit 4 and information on the measurement light Lb when it is emitted from the light emitting unit 2. The computing unit 7 performs calibration on the gas analysis apparatus 100 using the respectively calculated reference values when the zero gas is introduced and when the span gas is introduced. The calibration can be preferably performed at an interval of one hour, for example. The calibration can be performed each time a user instruction is given, or can be performed automatically and periodically.

According to the first embodiment, since the second reflector 5 and the switching unit 8 are arranged outside the gas flue wall 1a, a plurality of effects can be obtained as follows. It should be noted that, it is not necessary to obtain all of the below effects in the first embodiment, but it is sufficient to obtain only one or part of them.

1) The second reflector 5 and the switching unit 8 are not exposed to the sample gas Sg, which has a high temperature. Accordingly, it is possible to suppress the deterioration of the second reflector 5 and the switching unit 8, thereby reducing the frequency of replacing parts and thereby reducing the maintenance cost. It should be noted that in the present invention, in order to highly precisely perform the component concentration analysis (sampling), at least one of the correction or the calibration is performed. It is not necessary to set the temperature of the zero gas used for the correction to the same level as the temperature of the analysis target gas (i.e., the zero gas does not substantially absorb the measurement light regardless of the temperature). Accordingly, in this embodiment, it is possible to arrange the known substance containing unit 6 with the second reflector 5 outside the gas flue wall 1a. It should be noted that even if the known substance containing unit 6 is arranged with the second reflector 5 outside the gas flue wall 1a, it is possible to perform the calibration as described above.

2) The switching operation of the switching unit 8 makes it possible to selectively set a state in which the second reflector 5 is removed from the light path and a state in which the second reflector 5 is placed into the light path. Accordingly, it is possible to perform the component concentration analysis, the zero correction, the zero calibration, and the span calibration with one light receiving unit 4, without using the optical coupler and splitter for branching the one light beam into two light beams. As a result, it is possible to highly precisely perform the component concentration analysis without the effects from individual differences due to having two light receiving units, as in the conventional arts.

3) With one system (the system consisting of the light receiving unit 4 and the computing unit 7), it is possible to perform the component concentration analysis, the zero correction, the zero calibration, and the span calibration. Accordingly, it is possible to make the gas analysis apparatus 100, as a whole, compact with small number of parts, thereby reducing the manufacturing cost.

4) Since the second reflector 5 and the switching unit 8 are arranged outside the gas flue wall 1a, it is possible to exchange these parts easily.

Furthermore, the back-forward moving mechanism depicted in FIGS. 4, 5 employs a normally closed way. Specifically, when the air pressure is being supplied by the normal operation of the valves 85, 86, the air pressure removes the second reflector 5 from the light path against the elastic force of the spring 81, and the gas analysis apparatus 100 shifts to the gas concentration analysis mode (refer to FIG. 4). In contrast, when the supply of the air pressure is being shut off by the normal operation by the valves 85, 86, the elastic force of the spring 81 places the second reflector 5 into the light path, and the gas analysis apparatus 100 shifts to the zero correction mode or calibration mode (refer to FIG. 5). Furthermore, when the supply of the air pressure is being shut off due to abnormality such as a power failure, the elastic force of the spring 81 places the second reflector 5 into the light path, and the gas analysis apparatus 100 shifts to the zero correction mode or calibration mode (refer to FIG. 5). Accordingly, during the abnormality such as a power failure, the second reflector 5 performs a shutter function, thereby preventing the sample gas Sg from moving into a space near the light emitting unit 2 and the light receiving unit 4.

In addition, the back-forward moving mechanism depicted in FIGS. 6, 7 employs a normally opened way. In other words, when the air pressure is being supplied by the normal operation of the valves 85, 86, the air pressure places the second reflector 5 into the light path against the elastic force of the spring 810, and the gas analysis apparatus 100 shifts to the correction mode or calibration mode (refer to FIG. 7). In contrast, when the supply of the air pressure is being shut off by the normal operation of the valves 85, 86, the elastic force of the spring 810 removes the second reflector 5 from the light path, and the gas analysis apparatus 100 shifts to the gas concentration analysis mode (refer to FIG. 6). In addition, when the supply of the air pressure is being shut off due to abnormality such as a power failure, the elastic force of the spring 810 removes the second reflector 5 from the light path, and the gas analysis apparatus 100 shifts to the gas concentration analysis mode (refer to FIG. 6).

Second Embodiment

Figure 8:
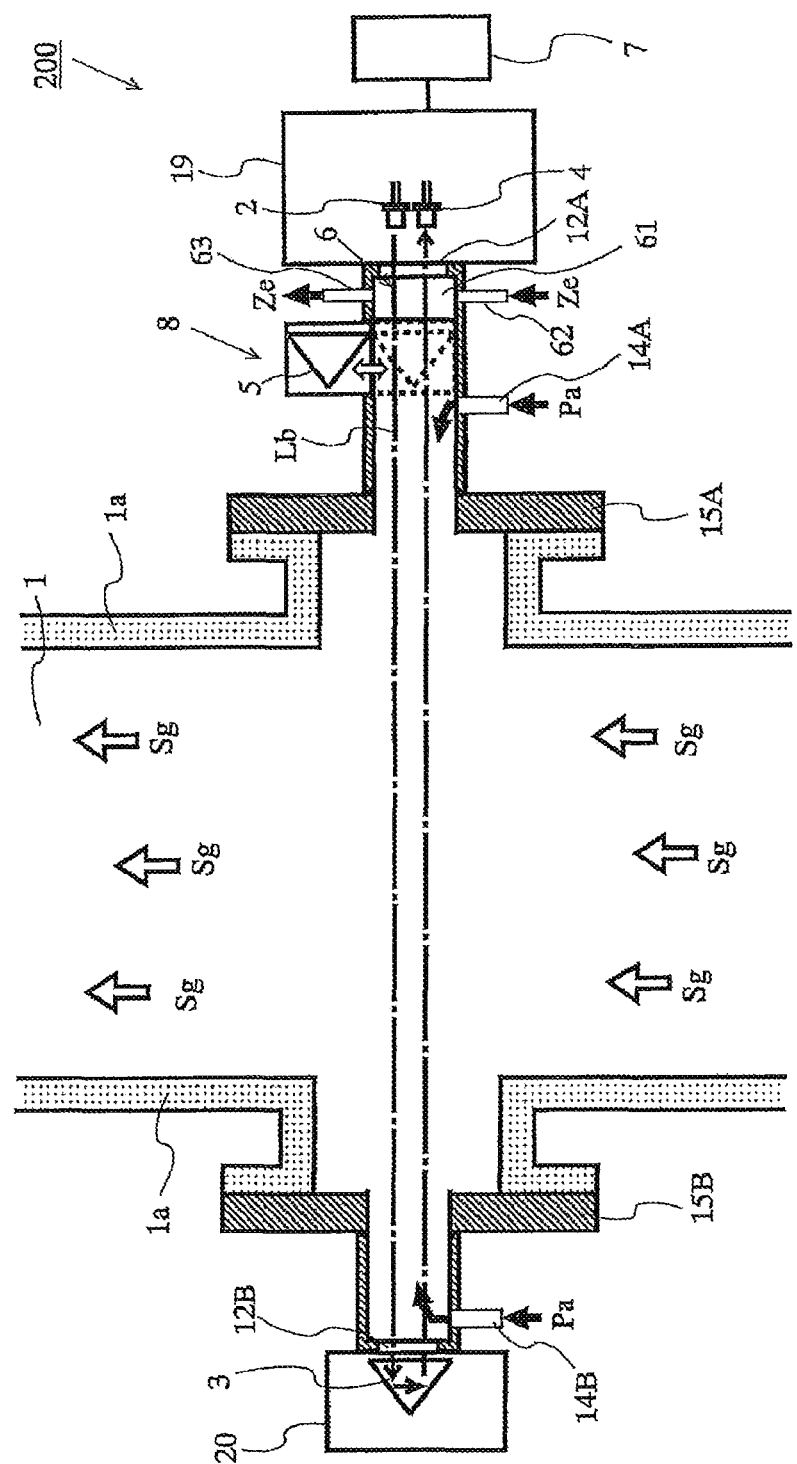
FIG. 8 is a sectional view for showing internal constituents of the gas analysis apparatus in the second embodiment, and is a view for showing the gas concentration analysis mode.
Figure 9:
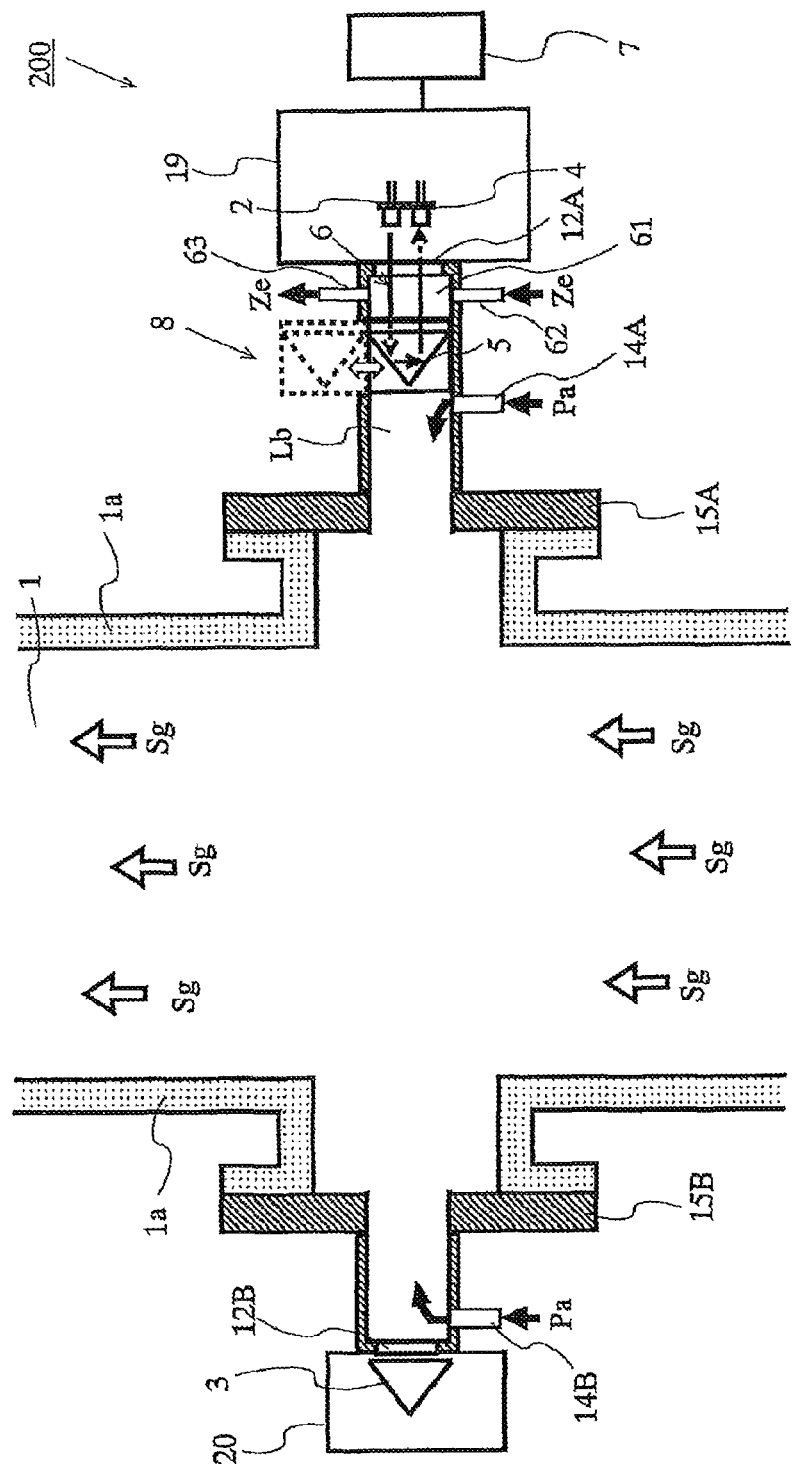
FIG. 9 is a sectional view for showing internal constituents of the gas analysis apparatus in the second embodiment, and is a view for showing the correction mode or the calibration mode.

Below, a gas analysis apparatus 200 according to the second embodiment will be described. The gas analysis apparatus 200 is a gas analysis apparatus of what is called open path type. FIG. 8 is a sectional view for showing internal constituents of the gas analysis apparatus in the second embodiment, and is a view for showing the gas concentration analysis mode. FIG. 9 is a sectional view for showing internal constituents of the gas analysis apparatus in the second embodiment, and is a view for showing the zero correction mode. The second embodiment will be explained by mainly focusing on points different from the first embodiment. The same structure as those of the first embodiment will not be explained, while the same reference symbols are assigned.

According to the second embodiment, as shown in FIGS. 8, 9, the gas analysis apparatus 200 is constituted by a first unit 19 and a second unit 20, which are formed separately and independently. The first unit 19 is attached to one side surface of the wall 1a of the gas flue, through which the sample gas Sg flows, and the second unit 20 is attached to another side surface of the gas flue wall 1a such that the first unit 19 and the second unit 20 face each other.

The first unit 19 includes a light emitting unit 2, a light receiving unit 4, a second reflector 5, a known substance containing unit 6, a computing unit 7, a switching unit 8, an optical window 12A, and a purge air introduction port 14A. The purge air introduction port 14A is configured to introduce purge air Pa into a space connected to the gas flue wall 1a just in front of the second reflector 5. The first unit 19 includes a tubular member 114 extending between the flange 15A and the light emitting unit 2 as well as the light receiving unit 4. The tubular member 114 accommodates the known substance containing unit 6 and the switching unit 8.

The second unit 20 includes the first reflector 3, the optical window 12B, and the purge air introduction port 14B. The purge air introduction port 14B introduces purge air Pa into a space connected to the gas flue wall 1a just in front of the optical window 12B.

Next, use of the gas analysis apparatus 200 will be described.

First, a case will be described in which a normal gas concentration analysis is performed.

A user gives an instruction to the computing unit 7 for performing the gas concentration analysis. Then, as shown in FIG. 8, the switching unit 8 removes the second reflector 5 from the light path of the measurement light Lb emitted from the light emitting unit 2. The measurement light Lb emitted from the light emitting unit 2 is transmitted through the sample gas Sg in the gas flue 1, and is reflected by the first reflector 3. The reflected measurement light Lb is transmitted through the sample gas Sg in the gas flue 1 again, and is received by the light receiving unit 4. When the measurement light Lb is transmitted through the sample gas Sg, part of the measurement light Lb is absorbed by the sample gas Sg. The computing unit 7 can acquire the amount of absorption of the measurement light Lb in the sample gas Sg, based on difference between information on the measurement light Lb obtained at the light receiving unit 4 and information on the measurement light Lb when it is emitted from the light emitting unit 2. The computing unit 7 can calculate concentration of certain components contained in the sample gas Sg, based on the amount of absorption.

Next, a case will be described in which the zero correction is performed.

A user gives an instruction to the computing unit 7 for performing the zero correction. Then, as shown in FIG. 9, the switching unit 8 places the second reflector 5 into the light path of the measurement light Lb emitted from the light emitting unit 2. The measurement light Lb emitted from the light emitting unit 2 is transmitted through the zero gas in the known substance containing unit 6, and is reflected by the second reflector 5. The reflected measurement light Lb is transmitted through the zero gas in the known substance containing unit 6 again, and is received by the light receiving unit 4. The computing unit 7 calculates a reference value of the zero correction, based on difference between information on the measurement light Lb obtained at the light receiving unit 4 and information on the measurement light Lb when it is emitted from the light emitting unit 2. The computing unit 7 performs the zero correction of the gas analysis apparatus 200 using the calculated reference value. The zero correction can be performed at an interval of one hour, for example. It should be noted that the zero correction can be preferably performed each time a user instruction is given, or can be performed automatically and periodically.

In the second embodiment too, since the second reflector 5 and the switching unit 8 are arranged outside the gas flue wall 1a, the same excellent effects are achieved as in the first embodiment.

Since the known substance containing unit 6 just has to be arranged outside the gas flue wall 1a, various modifications are possible. Below, those modifications will be explained.

In the above-described embodiments, the known substance containing unit 6 contains the zero gas or the span gas. However, instead of these, the known substance containing unit 6 may contain an optically transparent plate or an optical element that is perfectly transparent for the measurement light Lb or that limits the transmitted measurement light Lb by a predetermined amount.

In addition, in the above-described embodiment, the known substance containing unit 6 is arranged to be fixed in the probe tube 9 or the tubular member 114. However, instead of these, the known substance containing unit 6 may be configured to be able to move into or out of the probe tube 9 or the tubular member 114. In this case, in a state that the known substance containing unit 6 is arranged in the probe tube 9 or the tubular member 114, the correction or calibration of the analysis apparatus can be performed, and in a state that the known substance containing unit 6 is arranged out of the probe tube 9, the gas concentration analysis can be performed. As a moving-in-out mechanism, for example, the same structure as the above-described back-forward moving mechanism can be employed.

Furthermore, in the above-described embodiments, the known substance containing unit 6 is arranged in the probe tube 9 or the tubular member 114. However, instead of these, the known substance containing unit 6 may be arranged in the housing 11 of the optical unit or the housing of the first unit 19. In this case, it is possible to make the optical windows 12, 12A and the second reflector 5 close to each other in order to substantially close the gap therebetween.

Third Embodiment

Figure 10:
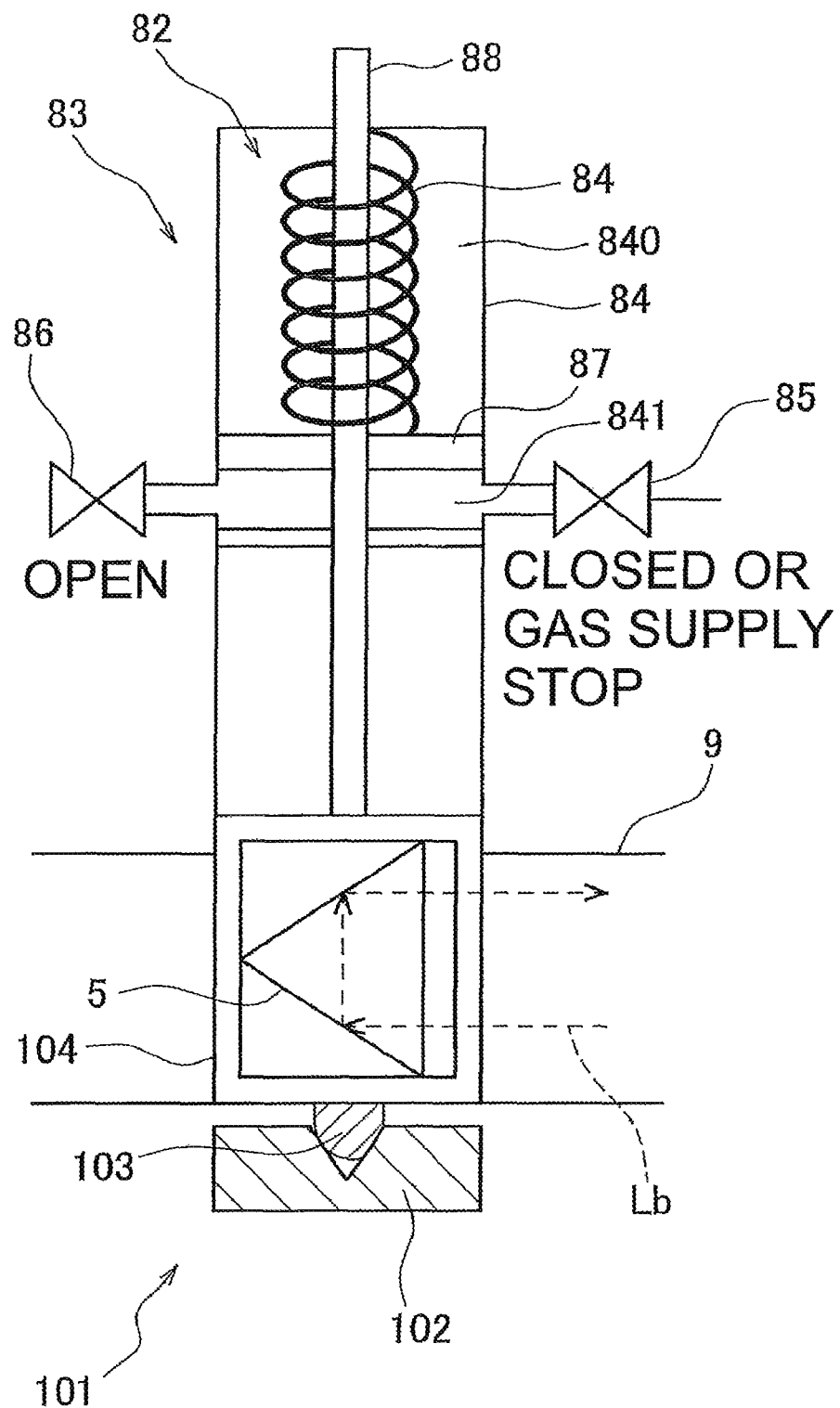
FIG. 10 is a sectional view for showing a structure of the switching unit in the third embodiment, and is a view for showing the correction mode or the calibration mode.
Figure 11:
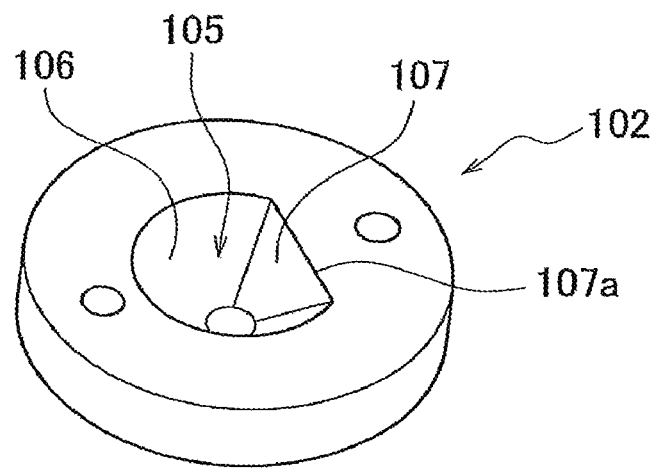
FIG. 11 is a perspective view of a bearing.
Figure 12:
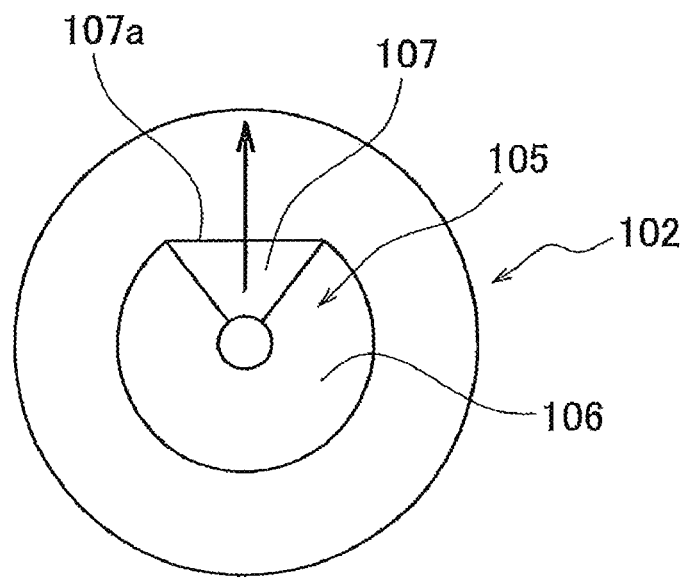
FIG. 12 is a plane view of a bearing.
Figure 13:
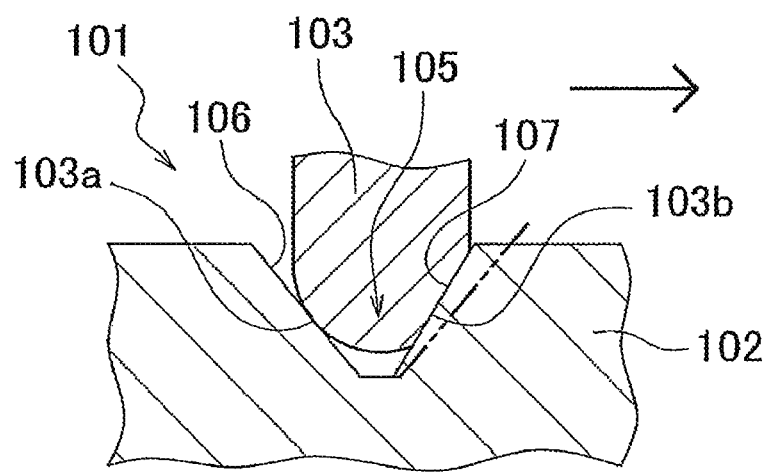
FIG. 13 is a partial enlarged view of FIG. 10.

Using FIG. 10 to FIG. 13, a third embodiment will be described. The third embodiment is different from the above-described embodiments only in a structure that supports the second reflector 5. FIG. 10 is a sectional view for showing a structure of the switching unit in the third embodiment, and is a view for showing the correction mode or the calibration mode. FIG. 11 is a perspective view of a bearing. FIG. 12 is a plane view of a bearing. FIG. 13 is a partial enlarged view of FIG. 10.

The second reflector 5 is supported by a mirror holder 104.

As shown in FIG. 10, in this embodiment, the back-forward moving mechanism includes a positioning mechanism 101. The positioning mechanism 101 adjusts the position of the second reflector such that the second reflector 5 has always the same direction and the same position when the air cylinder 84 places the second reflector 5 into the light path.

The positioning mechanism 101 is arranged below the second reflector 5 and a mirror holder 104, and is composed of a bearing 102, and a convex 103 provided at the mirror holder 104.

The bearing 102 is, as shown in FIG. 11, a plate member. The bearing 102 is formed with a concave 105 opening upward. The concave 105 has a generally conical shape. The concave 105 has a conical surface 106. The concave 105 is formed with a first plane 107, at a part along the circumferential direction, which extends from a portion inwards of the outer perimeter of the conical surface 106 toward a bottom portion. The first plane 107 has a shape of trapezoid whose width becomes narrower toward the bottom portion. It should be noted that an upper edge 107a of the first plane 107 is arranged on a side towards the light emitting unit 2 and the light receiving unit 4, and the upper edge 107a is perpendicular to the light path.

The convex 103 of the mirror holder 104 is generally spherical. The convex 103 has a spherical surface 103a. In addition, the convex 103 is formed with a second plane 103b along a part in the circumferential direction. The second plane 103b is formed in a way as if a part of the spherical surface is cut away toward inside, and its shape and size correspond to those of the first plane 107.

It should be noted that the first plane 107 and the second plane 103b are formed on a side toward which a reflecting surface of the second reflector 5 is desired to face (toward the light emitting unit 2 and the light receiving unit 4, as shown by arrow A).

In this apparatus, when the second reflector 5 is returned into the light path by the force from the air cylinder 84, the positioning mechanism 101 positions the second reflector 5 in the same orientation and at the same position. Especially, since it is not necessary to have a complicated structure for positioning or a special energy source, the cost is reduced.

More specifically, if the air cylinder 84 pushes the second reflector 5 and the mirror holder 104 toward the bearing 102, the convex 103 of the mirror holder 104 fits into the concave 105 of the bearing 102. At this time, the above-described shape allows the convex 103 to move relative to the concave 105 in the vertical direction while being allowed to move in the rotational direction. Finally, the second plane 103b of the convex 103 abuts against the first plane 107 of the concave 105 in a complementary manner. In this state, the convex 103 can neither move relative to the concave 105 in the moving direction nor the rotational direction. In this way, the second reflector 5 is always positioned in the same orientation and at the same position.

Particularly, only by the operation of the air cylinder 84 pressing the second reflector 5, the positioning mechanism 101 can precisely determine the orientation and the position in the moving direction of the second reflector 5.

Figure 14:
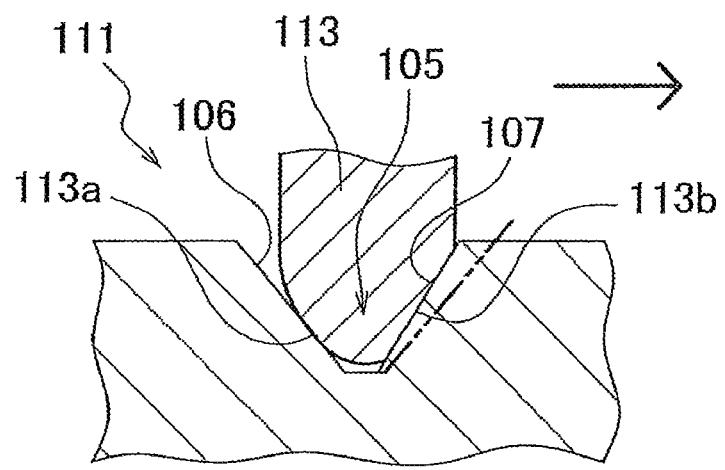
FIG. 14 is a sectional view of a positioning mechanism as a first modification of a third embodiment.

As a first modification of the third embodiment, FIG. 14 shows the positioning mechanism 101. FIG. 14 is a sectional view of a positioning mechanism, as a first modification of the third embodiment.

The structure of the concave 105 is the same as that of the above-described embodiment.

The convex 113 of the mirror holder 104 has a generally conical shape. The convex 113 has a conical surface 113a. In addition, the convex 113 is formed with a second plane 113b along a part in the circumferential direction. The second plane 113b is formed in a way as if a part of the conical surface 113a is cut away toward inside, and its shape and size correspond to those of the first plane 107.

If the air cylinder 84 pushes the second reflector 5 and the mirror holder 104 toward the bearing 102, the convex 113 of the mirror holder 104 fits into the concave 105 of the bearing 102. At this time, the above-described shape allows the convex 113 to move relative to the concave 105 in the vertical direction while being allowed to move relative to the concave 105 in the rotational direction. Finally, the second plane 113b of the convex 113 abuts against the first plane 107 of the concave 105 in a complementary manner. In this state, the convex 113 can neither move relative to the concave 105 in the moving direction nor the rotational direction. In this way, the second reflector 5 is always positioned in the same direction and at the same position.

Particularly, by only the operation of the air cylinder 84 pressing the second reflector 5, the positioning mechanism 101 can precisely determine the direction and the position in the moving direction of the second reflector 5.

Figure 15:
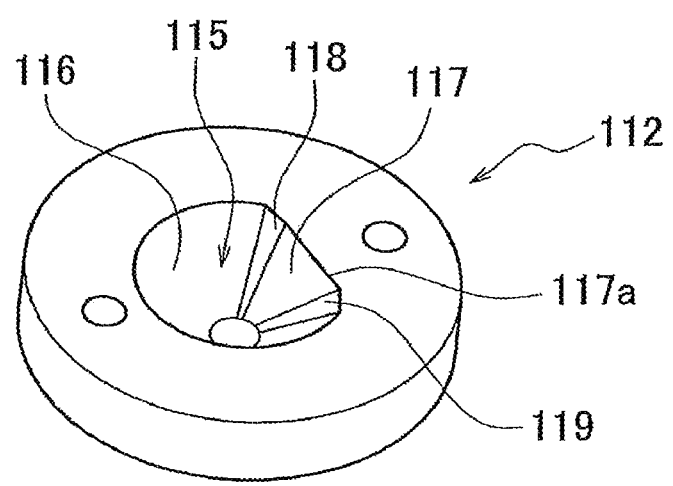
FIG. 15 is a perspective view of a bearing in a second modification in the third embodiment.

As a second modification of the third embodiment, FIG. 15 shows a bearing 112. FIG. 15 is a perspective view of a bearing in a second modification in the third embodiment.

The bearing 112 is, as shown in FIG. 15, a plate member. The bearing 112 is formed with a concave 115 opening on the upper surface. The concave 115 has a generally conical shape. The concave 115 has a conical surface 116. The concave 115 is formed with a first plane 117, which is formed along a part in the circumferential direction and extends from a part inwards of the outer perimeter of the concave 115 toward the bottom portion. The first plane 117 has a shape of trapezoid whose width becomes narrower toward the bottom portion. It should be noted that an upper edge 117a of the first plane 117 is arranged on a side towards the light emitting unit 2 and the light receiving unit 4, and the upper edge 117a is perpendicular to the light path.

In this modification, a third plane 118 and a fourth plane 119 are formed on two sides of the first plane 117 in the circumferential direction. The third plane 118 and the fourth plane 119 has a shape of trapezoid extending toward the bottom portion, whose width becomes narrower toward the bottom portion, like the first plane 117. However, the circumferential width of the third plane 118 and the fourth plane 119 is narrower than the circumferential width of the first plane 117.

Although not shown in the figures, a convex of the mirror holder has surfaces having a shape that can abut against the first plane 117, the third plane 118, and the fourth plane 119, in a complementary manner.

Due to the above-described structure, in this modification, the same effects can be achieved as in the above-described embodiment.

Other Embodiments

Although embodiments of the present invention are described above, the present invention is not limited to these embodiments and can be variously modified within the scope without deviating from the spirit of the present invention. In particular, the plurality of embodiments and variations described in this specification can be arbitrarily combined as necessary.

For example, the third embodiment can be combined with the first embodiment (including the modifications), or can be combined with the second embodiment (including the modifications).

In the above-described embodiments, the air cylinder is used as a back-forward moving mechanism. However, as long as the back-forward moving mechanism can remove the second reflector from the light path and place second reflector into the light path, another mechanism can be used. For example, instead of the air cylinder, an oil hydraulic cylinder can be used. In addition, instead of a cylinder, a motor can be employed. In this case, for example, a linear motor or a combination of a rotary motor and a mechanism that converts the rotational force into a force in the straight direction can be used.

INDUSTRIAL APPLICABILITY

A measurement unit and a gas analysis apparatus according to the present invention can be useful as a measurement unit and a gas analysis apparatus that can analyze the sample gas precisely compared to the conventional ones.

REFERENCE SIGNS LIST

100, 200 gas analysis apparatus
1 gas flue
1a gas flue wall
2 light emitting unit
3 first reflector
4 light receiving unit
5 second reflector
6 known substance containing unit
7 computing unit
8 switching unit
81 spring
82, 820 spring mechanism
83, 830 air pressure mechanism
84 air cylinder
840 first air chamber
841 second air chamber
85 supply valve
86 exhaust valve
87 piston
88 rod
9 probe tube
91 introduction hole
11 housing of the optical unit
12 optical window
14, 16 purge air introduction port
15 flange
17, 18 hole
19 first unit
20 second unit
Lb measurement light
Sg sample gas

The invention claimed is:

1. A gas analysis apparatus configured to analyze concentrations of element gases in a sample gas flowing in a flue, the gas analysis apparatus comprising:
a light-emitting unit arranged outside a wall of the flue and configured to apply a measurement light to the sample gas;
a first reflector configured to reflect the measurement light applied from the light-emitting unit and that has been transmitted through the sample gas;
a light-receiving unit arranged in the vicinity of the light-emitting unit and outside the wall of the flue, and configured to receive the measurement light reflected by the first reflector;
a second reflector arranged outside the wall of the flue and configured to reflect the measurement light to the light-receiving unit;
a known substance containing unit arranged in a space region along a light path between the light-emitting unit and the second reflector and between the second reflector and the light receiving unit, the known substance containing unit containing a known substance that allows the measurement light applied from the light-emitting unit not to be attenuated or to be attenuated by a predetermined amount;
a computing unit configured both to analyze the concentrations of the element gases in the sample gas using the measurement light reflected by the first reflector and to perform at least one of a correction and a calibration with the known substance using the measurement light reflected by the second reflector; and
a switching unit arranged outside the wall of the flue and configured to remove the second reflector from the light path when performing the analysis of the concentrations of the element gases and to place the second reflector into the light path when performing at least one of the correction and the calibration.

2. The gas analysis apparatus according to claim 1, wherein the switching unit includes a back-forward moving mechanism configured to selectively remove the second reflector from the light path and to selectively place the second reflector into the light path, respectively.

3. The gas analysis apparatus according to claim 2, wherein the back-forward moving mechanism includes an air cylinder or a motor.

4. The gas analysis apparatus according to claim 3, wherein the back-forward moving mechanism includes a positioning mechanism configured to arrange the second reflector in a same direction and at a same position every time when the second reflector is placed into the light path through an operation of the air cylinder or the motor.

5. The gas analysis apparatus according to claim 4, wherein the positioning mechanism includes a holder fixed to the second reflector and a bearing configured to hold the holder,
wherein the bearing has a conical concave portion, the holder has a conical or spherical convex portion, the concave portion of the bearing has a first plane with a trapezoidal shape that is formed in a part of the concave portion, a side of the first plane at a bottom of the concave portion being narrower than that at a top of the concave portion, and the conical or spherical convex portion has a second plane configured to abut against the first plane in a complementary manner.

6. The gas analysis apparatus according to claim 2, wherein the second reflector, when placed in the light path, serves as a shutter that separates a space near the flue from a space near the known substance containing unit.

7. The gas analysis apparatus according to claim 6, wherein the back-forward moving mechanism includes an air cylinder or a motor.

8. The gas analysis apparatus according to claim 7, wherein the back-forward moving mechanism includes a positioning mechanism configured to arrange the second reflector in a same direction and at a same position every time when the second reflector is placed into the light path through an operation of the air cylinder or the motor.

9. The gas analysis apparatus according to claim 8, wherein the positioning mechanism includes a holder fixed to the second reflector and a bearing configured to hold the holder,
wherein the bearing has a conical concave portion, the holder has a conical or spherical convex portion, the concave portion of the bearing has a first plane with a trapezoidal shape that is formed in a part of the concave portion, a side of the first plane at a bottom of the concave portion being narrower than that at a top of the concave portion, and the conical or spherical convex portion has a second plane configured to abut against the first plane in a complementary manner.

10. The gas analysis apparatus according to claim 1, wherein the second reflector, when placed in the light path, serves as a shutter that separates a space near the flue from a space near the known substance containing unit.

11. The gas analysis apparatus according to claim 10, wherein the back-forward moving mechanism includes an air cylinder or a motor.

12. The gas analysis apparatus according to claim 11, wherein the back-forward moving mechanism includes a positioning mechanism configured to arrange the second reflector in a same direction and at a same position every time when the second reflector is placed into the light path through an operation of the air cylinder or the motor.

13. The gas analysis apparatus according to claim 12, wherein the positioning mechanism includes a holder fixed to the second reflector and a bearing configured to hold the holder,
wherein the bearing has a conical concave portion, the holder has a conical or spherical convex portion, the concave portion of the bearing has a first plane with a trapezoidal shape that is formed in a part of the concave portion, a side of the first plane at a bottom of the concave portion being narrower than that at a top of the concave portion, and the conical or spherical convex portion has a second plane configured to abut against the first plane in a complementary manner.

14. The gas analysis apparatus according to claim 1, wherein the known substance containing unit includes an optically transparent cell.

15. The gas analysis apparatus according to claim 1, further comprising a probe tube with a cylindrical shape having introduction openings through which the sample gas is introduced into the probe tube,
wherein the light-emitting unit applies the measurement light to the sample gas in the probe tube.

16. The gas analysis apparatus according to claim 15, wherein the probe tube includes a front end portion placed inside the wall and a base end portion placed outside the wall, and
the first reflector is arranged at the front end portion of the probe tube, and the second reflector is arranged at the base end portion of the probe tube.

17. The gas analysis apparatus according to claim 16, wherein the known substance containing unit is placed at the base end portion of the probe tube.

18. The gas analysis apparatus according to claim 1, wherein the first reflector is arranged outside the wall that is opposite to a portion where the second reflector is arranged in the flue.

* * * * *